(12) United States Patent
List

(10) Patent No.: US 8,086,965 B2
(45) Date of Patent: Dec. 27, 2011

(54) METHOD AND SYSTEM FOR GENERATION OF A USER INTERFACE

(75) Inventor: Steffen List, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 709 days.

(21) Appl. No.: 11/930,463

(22) Filed: Oct. 31, 2007

(65) Prior Publication Data

US 2008/0104533 A1    May 1, 2008

(30) Foreign Application Priority Data

Oct. 31, 2006   (DE) .......................... 10 2006 051 447

(51) Int. Cl.
  *G06F 3/14* (2006.01)
  *G06F 3/17* (2006.01)
(52) U.S. Cl. ........ 715/771; 715/762; 715/781; 715/863; 600/300; 600/437; 434/262; 463/36
(58) Field of Classification Search .......... 715/200–277, 715/863, 762, 769, 781, 792; 700/701–866; 709/201–229; 705/50–79, 2; 345/30–111; 348/206–231.9; 600/437, 300; 434/262; 463/36

See application file for complete search history.

(56) References Cited

U.S. PATENT DOCUMENTS

| | | | |
|---|---|---|---|
| 5,596,702 A | 1/1997 | Stucka et al. | |
| 5,910,799 A | 6/1999 | Carpenter et al. | |
| 7,371,067 B2 * | 5/2008 | Anderson et al. | 434/262 |
| 7,516,416 B2 * | 4/2009 | Viswanathan et al. | 715/781 |
| 2002/0184055 A1 * | 12/2002 | Naghavi et al. | 705/2 |
| 2003/0058280 A1 | 3/2003 | Molinari et al. | |
| 2004/0015079 A1 * | 1/2004 | Berger et al. | 600/437 |
| 2005/0229110 A1 | 10/2005 | Gegner et al. | |
| 2007/0232866 A1 * | 10/2007 | Nephin et al. | 600/300 |
| 2010/0011305 A1 * | 1/2010 | Ullom et al. | 715/762 |
| 2010/0138798 A1 * | 6/2010 | Wilson et al. | 715/863 |
| 2010/0151946 A1 * | 6/2010 | Wilson et al. | 463/36 |

* cited by examiner

*Primary Examiner* — Ruay Ho
(74) *Attorney, Agent, or Firm* — Schiff Hardin LLP

(57) ABSTRACT

In a method and system for generating a user interface for at least one medical application to be implemented by a medical apparatus, a designation of the medical application to be implemented is provided to a computerized processor, which automatically then registers only control elements for inclusion in the user interface that are relevant for controlling the designated medical application. The processor automatically positions control elements, individually or in groups, in the user interface at a display screen according to configurable positioning criteria that minimize at least one of space on the display screen occupied by the control elements, and user steps to activate the control elements, to form the user interface.

17 Claims, 3 Drawing Sheets

FIG 4
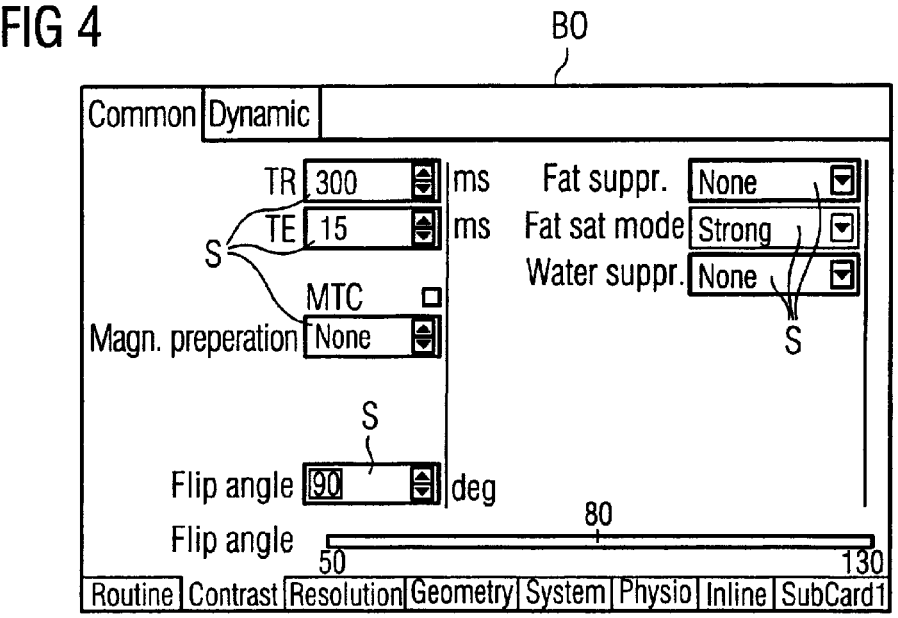
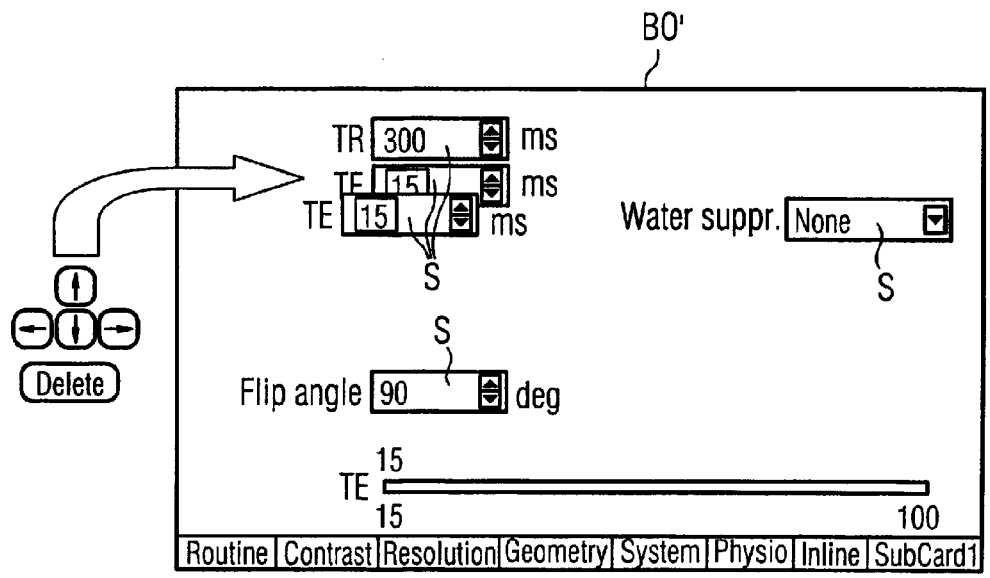

METHOD AND SYSTEM FOR GENERATION OF A USER INTERFACE

BACKGROUND OF THE INVENTION

1. Field of the Invention

The present invention concerns data processing and medical technology and in particular concerns a method, a system, and a storage medium encoded with a computer program for designing user interfaces for complex medical technology apparatuses such as, for example, magnetic resonance tomography systems.

2. Description of the Prior Art

A number of settings and configurations that require different user interfaces dependent on the respective application are necessary to control a complex system such as a magnetic resonance tomography system. If one envisions the number of possible applications for a magnetic resonance apparatus (for example sequence techniques, post-processing applications, etc.) that each require different user inputs as control elements for the application (such as, for example, time specifications, details for the post-processing steps, upper limits and lower limits, etc.), it is clear that many parameters must be presented on the user interface. The conventional representation can be very unclear because parameters that are not of importance for particular application still are shown. A conventional user interface for the presentation of MR measurement or post-processing parameters is essentially static and primarily shows a superset of all parameters available in principle with regard to the MR apparatus. As is known from other systems in the prior art, respective parameters can be displayed b a manner known as parameter cards. In connection with an MR apparatus, multiple hundreds of parameters that are distributed across 25 parameter cards would have to be displayed. Surveying the displayed parameters is therefore a very time-intensive and error-prone process and overall results in a very laborious operation. Each application that should be executed in connection with the MR apparatus requires different parameter sets. In conventional systems it has not been possible to adapt the user interface to the respective application and to display, in an ergonomically reasonable arrangement, only the parameters that are relevant for the respective application. For example, a particular application (such as angiography) requires only a few specific parameter inputs as control commands by the user, but these are conventionally scattered on many different cards. Most other parameters on these parameter cards could be disregarded for this specific case.

Methods for adaptation or modification of user environments or user interfaces are known.

EP 0 801 342 B1 teaches a method for the adaptation of a user environment solely on the basis of a geographic position in order to be able to display matching display symbols in the user environment.

U.S. Pat. No. 5,596,702 discloses a method for common usage of user interfaces through software applications in that existing user interfaces are modified only with regard to uniform graphical design and uniform functionality.

SUMMARY OF THE INVENTION

An object of the present invention is to provide a way to improve a user interface for controlling applications for a complex medical technology apparatus in particular for a magnetic resonance tomography apparatus, in particular to dynamically and flexibly focus on the respective application and to optimize with regard to the space requirement on the screen.

This object is achieved by a method for generation of a user interface for at least one medical application from a set of different applications for a medical apparatus, or for controlling the apparatus including the steps of determining the application for which the user interface should be generated, detecting control elements that are relevant for controlling the specific application, positioning the relevant control elements individually and/or in control groups on a screen according to configurable positioning criteria, such that an optimal layout results for the control elements, in particular with regard to a space requirement.

In the following the basic concepts that are used in the framework of this invention are explained in brief.

The user interface is a typical user interface that is used in data processing systems. It is typically graphical and has control elements for controlling the respective application such as icons, cards or folders that can be activated by suitable computer accessories such as, for example, via a keyboard or via a mouse.

The specification of the present invention primarily concerns a magnetic resonance tomography apparatus as a medical apparatus. X-ray apparatuses, computed tomography apparatus or other imaging medical technology apparatuses on which applications should be executed are also possible.

The control elements are elements on the user interfaces that are designed for, among other things, controlling the application. They translate a user input (via keyboard, mouse or other means) into control signals for the respective application.

In order to enable easier handling for the user, individual control elements can be combined into control groups. These are then presented on the user interface in a structured or consolidated manner. For example, if the control elements are parameter input possibilities or other textual control elements, a control group can be a group of a number of control elements that is displayed as a folder or index card on the user interface. The structuring of the control elements can ensue according to pre-configurable structuring criteria. The control elements that exhibit a connection in terms of content are normally combined in one card. Moreover, it is possible to also recognize temporal correlations and to group together such control elements that must be activated by the user in successive steps. This leads to an easier and more efficient handling of the application.

As noted above in a control group is advantageously fashioned in the form of a card or a folder. A number of control elements that relate to one another in terms of content are consolidated here.

The control elements and/or of the control groups are positioned on the screen at optimal positions. This likewise typically ensues according to configurable positioning criteria. The positioning criteria are advantageously optimized with regard to space and/or operation expenditure, but further positioning criteria can also be used. This represents an advance in comparison to methods known from the prior art, since previously no selection of relevant control elements could be made, such that the user was confronted with a number of control elements and thus operation and navigation among these elements could be executed only in a difficult and time-consuming manner.

The structuring criteria and/or the positioning criteria can be pre-configurable.

In an embodiment of the invention, the control elements are a graphical representation for a parameter input. This can ensue in the form of textual inputs, inputs by means of keyboard and/or mouse or other accessories. The parameter inputs advantageously serve for controlling an application process (post-processing, adjustments in an angiography, control of a magnetic resonance tomography apparatus, etc.). The control elements are typically activated by a corresponding using input of a user. It is alternatively possible to activate the control elements by reading data out from other modules via an interface and for control using a decision action.

A difference from the prior art is that only the control elements and/or the control groups that are relevant for the respective application are presented on the user interface. The user thus is not confronted with control elements that are without importance for the application to be currently implemented.

In a further embodiment of the invention a reference is associated with a user interface generated for at least one application, by means of which reference the user interface can be retrieved and/or can be executed at a later point in time, in particular upon execution of the application. The association normally ensues via a name and is unambiguous. In other words, a generated user interface can be unambiguously selected or, respectively, determined via a name associated with it. This procedure is also designated as an ASSIGN procedure. All generated user interfaces and the respective names associated with them are typically stored in a corresponding data structure. The user thus can obtain an overview of which user interfaces can be selected in principle. Moreover, it is possible that a specific generated user interface is selected for an application is selected from a set of user interfaces. Here the user can also select from pre-configurable names. As soon as the user has selected a user interface for use, this is activated and presented on the screen. This procedure is also designated as a USE procedure. A high flexibility can be achieved with this solution, by allowing a number of user interfaces that are optimally designed for the respective usage or application to be selected and by allowing the point in time for activation of a user interface to be arbitrarily determined by the user.

In principle it is also possible for only one user interface to be generated for a respective usage or application, as is known in the prior art; but according to the invention a number of user interfaces can be respectively generated for a number of applications. This is particularly of importance in the medical technology environment since a magnetic resonance apparatus requires a very complex control that is based on a wide variety of different applications. Moreover, the respective applications can be applied in different medical contexts and by different persons. Different control elements or parameters may be necessary depending on the context or person, such that it is meaningful to also generate a number of user interfaces for the same application. An n:n relation thus arises between generated user interfaces and associated applications. This affords further degrees of freedom in the control of the medical apparatus.

In another embodiment of the invention, the method starts with an existing user interface and alters (in particular expands or limits) the presented control elements and/or the presented control groups thereof. Upon generation of a new user interface, the user does not have to unnecessarily reconfigure already-existing control elements again, but rather can already start from predefined elements. This produces a significant time gain in the generation of user interfaces. Moreover, a safety aspect is also achieved because the user is made aware of necessary control elements for the respective application, and thus these elements cannot be accidentally omitted in the generation of the user interface for that application.

In some special cases, it may be useful to generate a wholly new user interface and not to start from an already existing interface. In this case the control elements are registered that are necessary for control of the respective application. These are then structured or positioned such that an optimal layout of the user interface results overall. As explained in the preceding, such a complete reconfiguration is useful when, for example, a new application should be integrated into the system.

An important aspect of the inventive solution is that a change between different user interfaces for the same application is also possible at the time of execution. Scenarios thus can be covered that, for example, concern a user change or another change in the context of the application execution. The application does not have be restarted again, which increases the performance of the system overall.

Normally the control elements are hierarchically structured and include sub-control elements, in particular sub-cards. The number of the hierarchy levels is thereby not limited. The grouping or structuring of the relevant control elements of the generated user interface is advantageously executed such that an optimally easy and fast utility for the user is achieved. In contrast to previous methods from the prior art, the user must only navigate within the relevant control elements, and this navigation is made easier because the control elements are optimally arranged for the particular execution or operation at hand.

In a further embodiment of the invention, the registration of relevant control elements (thus of control elements that are necessary to control the respective application) ensues automatically by the respective application being determined or identified and access to storage structures, in which all control elements are stored that are relevant to each application, is thereupon executed. The registration of the relevant control elements thus ensues in a wholly automatic manner, but it is still possible to also provide manual or semi-automatic registration procedures that assist the user in the selection of relevant control elements via a pre-selection (for example presented in the form of menus).

In principle all or selected method steps are executed automatically. The positioning of the control elements on the screen should in particular be executed automatically, such that an optimized layout results. In the generation of the user interface the user here has the option to directly intervene in the positioning procedure, but does not necessarily have to do so.

In a further embodiment of the invention the inventive method includes the additional step of presenting the generated user interface with the control elements selected as relevant for controlling the application.

The user that can immediately monitor the automatically-generated user interface, since this is immediately displayed. Should inconsistencies exist, it is thus possible to cause the method to be executed again with altered generating conditions and to then store the procedure (association of the generated interface with regard to the application).

Thus a customized user interface can be achieved in accordance with the invention for each application case, the operation of this customized user interface being significantly more ergonomic, faster and simpler since only the respective relevant parameters (for example measurement and/or post-processing parameters) are displayed. Since the layout is optimized with regard to the relevant parameters and, usually, the parameters frequently match a single parameter card, no card changes are necessary. The handling is thus easier for the user and the orientation time for inexperienced users can be reduced, since they are only confronted with the relevant parameters. Overall the screen space for the presentation of the control elements can be minimized.

With regard to standard applications, automatically-generated standard user interfaces can be used. These can be used as a default user interface, so to speak. Standard parameters are used for generation of a default user interface. It can then be set how long this default user interface is used (whether it is used only temporarily and is then replaced, for example by a specific interface).

As already explained in the preceding, the registration of relevant control elements can ensue either automatically or manually. Either specific data sets are read that include a listing of relevant control elements for a respective application, or the user manually inputs the relevant control elements via a suitable interface. In the medical field there are normally a set of parameters that are of importance for each application. This parameter set is known as a "protocol" and constitutes a directive for the execution of the respective application. Such settings must be made for every single parameter. The registration of the control elements ensues centrally and/or dependent on the protocol. For example, protocol-specific user interfaces can thus replace the conventional generic user interfaces.

The above object also is achieved in accordance with the invention by a system for generation of a user interface for at least one medical application from a set of applications for a medical apparatus, in particular for a magnetic resonance tomography apparatus, having at least one application determination module that is fashioned to determine the application for which the respective user interface should be generated, at least one registration module that is designed to register control elements that are relevant for the application determined by the determination module, and at least one positioning module that is designed to present the relevant control elements and/or relevant control elements consolidated in control groups on a screen according to configurable positioning criteria, such that an optimal layout results, the positioned control elements respectively forming an interface for the application.

The above object also is achieved in accordance with the invention by a computer-readable medium encoded with a data structure that, when loaded into a computer, causes the computer to implement the method described above, including all embodiments thereof.

BRIEF DESCRIPTION OF THE DRAWINGS

FIG. 4 shows an exemplary representation of a user interface newly generated according to the invention with a number of cards and sub-cards (shown on the lower half of the page) based on an existing user interface (shown on the upper half of the page).

DESCRIPTION OF THE PREFERRED EMBODIMENTS

The inventive method seeks to generate a user interface BO automatically, dependent on the respective application to be implemented via the user interface BO.

For this purpose, in a first step the application is determined for which the user interface BO should be generated. Items known as control elements S are subsequently registered, preferably automatically. The control elements S are essentially parameter input options that are presented as elements on the user interface BO. As is apparent from the figures, these can either be fields for a textual or numerical input, selection possibilities from a menu representation, or other control elements that can be activated by a user input, for example by a keyboard, mouse or other computer input components. In an embodiment of the invention, the respective control elements S are to be structured, grouped or consolidated into control groups. A control group is typically what is known as a parameter card (also called a folder).

According to the invention, the control elements are selected from a set of control elements S that are possible in principle, such control elements S being relevant for the respective, determined application. An automatic positioning of the relevant control elements on a screen according to configurable positioning criteria thereupon ensues, such that an optimal screen layout is obtained. The positioning criteria are advantageously optimized and designed with regard to space requirement and/or operator effort. Through this feature only the relevant control elements S are presented on the screen, whereby the control elements S, or the respective control groups, are positioned such that an optimal layout is obtained. The user is confronted only with the necessary parameter query options that furthermore are positioned such that an optimally ergonomic input is possible.

Figure 1:
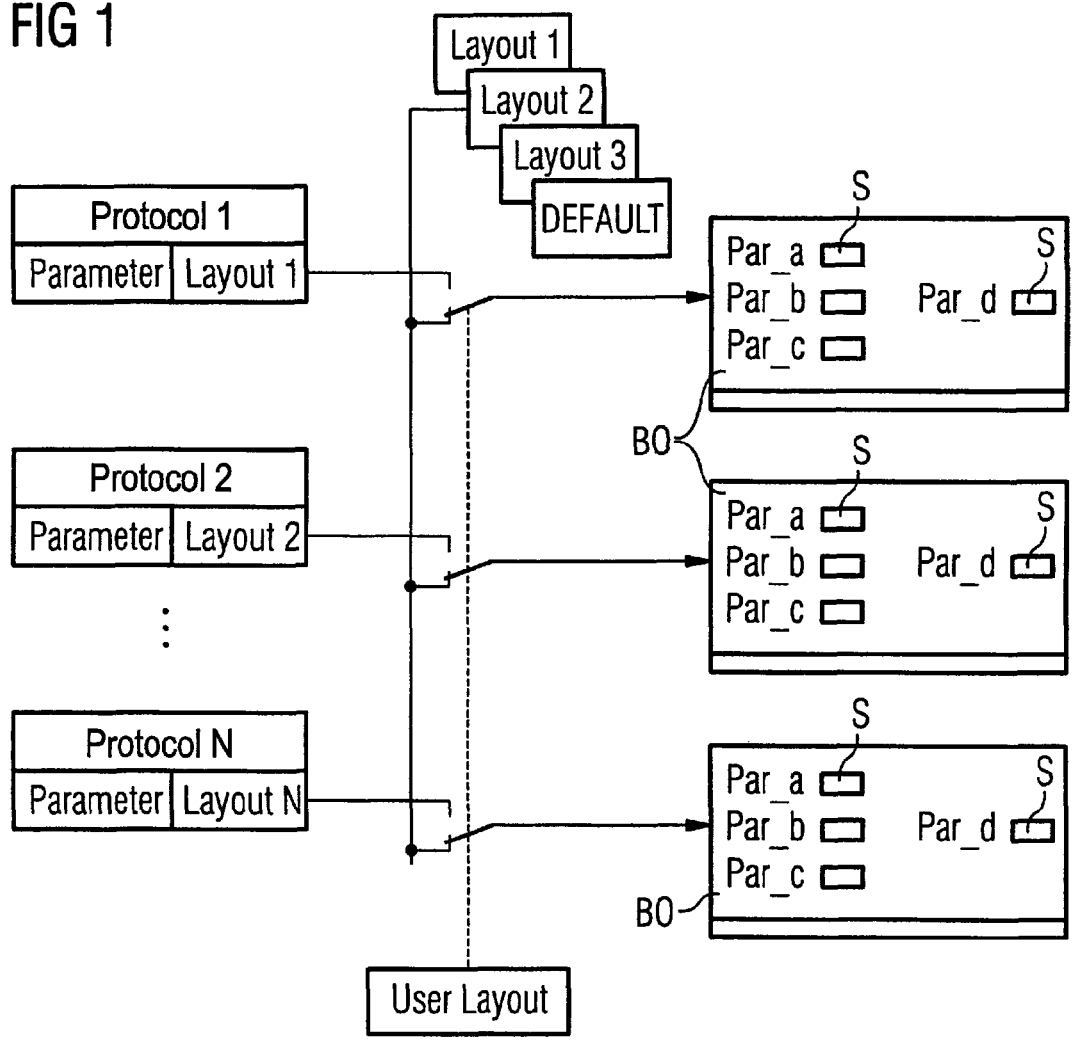
FIG. 1 is an overview representation for generation of a user interface using different protocols and using different layout data, according to the invention.

The interlinking of individual inventive modules into automatically optimized layouts of a user interface BO ensues is shown as an overview in FIG. 1. Different protocols (protocol 1, 2, N, . . . ) that embody a specification with regard to the parameters and the layout in this regard are shown on the left side. Execution of the method involves accessing a databank in which layout data are centrally stored. In addition to user-specific interfaces BO, default user interfaces are also stored therein. Based on the respective association, a user interface BO is inventively automatically generated that is shown on the right side of FIG. 1. In this case the control elements S (parameters Par_a, Par_b, Par_c and Par_d) are shown. The positioning of the control elements S advantageously ensues such that a minimal space demand is required on the screen. The result of the method is thus a visible user interface BO that contains different parameter card stacks, as is shown in the right three boxes in FIG. 1. FIG. 1 thus shows what is known as a USE mode, in which a user determines a specific layout (for example by specification of a layout name) that then appears as a layout for all open protocols or applications. As an alternative to centrally stored layout data, user-specific data can be used in the generation of the user interface BO, as is likewise indicated in FIG. 1 by the central lower boxes. User-specific data sets can be stored and/or administered ("User Layout 1").

According to one aspect (not shown), the USE mode can also be deactivated or shut down by a suitable deactivation mode (for example a predefined key or key combination). The layout information of each individual protocol is then used again. In principle—and in the event that it is desired—the respectively generated user interface BO could then appear differently for each protocol.

At runtime the user can select the user interface BO that is suitable for the application. This normally ensues by the user specifying or selecting the respective layout name (designated with Layout 1, Layout 2, Layout 3, . . . , Default Layout in FIG. 1, for example) in a central index. The layout selected by the user is then used for generation of the user interface BO. This pertains to the aforementioned USE mode of the inventive solution. The layout selected by the user is thereby used while the information in the protocol for generation of the user interface BO is ignored, but the protocol information is not altered. The result is that the layout specified by the user appears in all opened protocols.

In an alternative embodiment of the invention, new layout data are bound (linked) to a specific protocol. The control elements S (in particular the parameters) are then bound to at least one selected layout. The previous protocol-specific layout data are ignored in this case and no longer used, but rather are replaced by the newly selected layout. An increased flexibility thus is achieved by making possible a dynamic association of user interface variants with the applications. If a specific layout should be linked to a specific application, or should be associated therewith, it is thus adjustable to what extent this association should ensue. For example, it is possible to provide this association with a temporally limited context (for example only temporarily), or in a structurally limited context (for example only for specific hospital departments), or only in a functionally limited context (only for specific applications). The scope of the range of validity of an inventively generated user interface BO thus can be variably adjusted.

It is also possible to use predefined default layouts that are preset upon delivery of the respective product that will be operated by the interface. This improves the familiarization time given a new product and can simulate, as a special case, the previously familiar user interface from old software versions.

Figure 2:
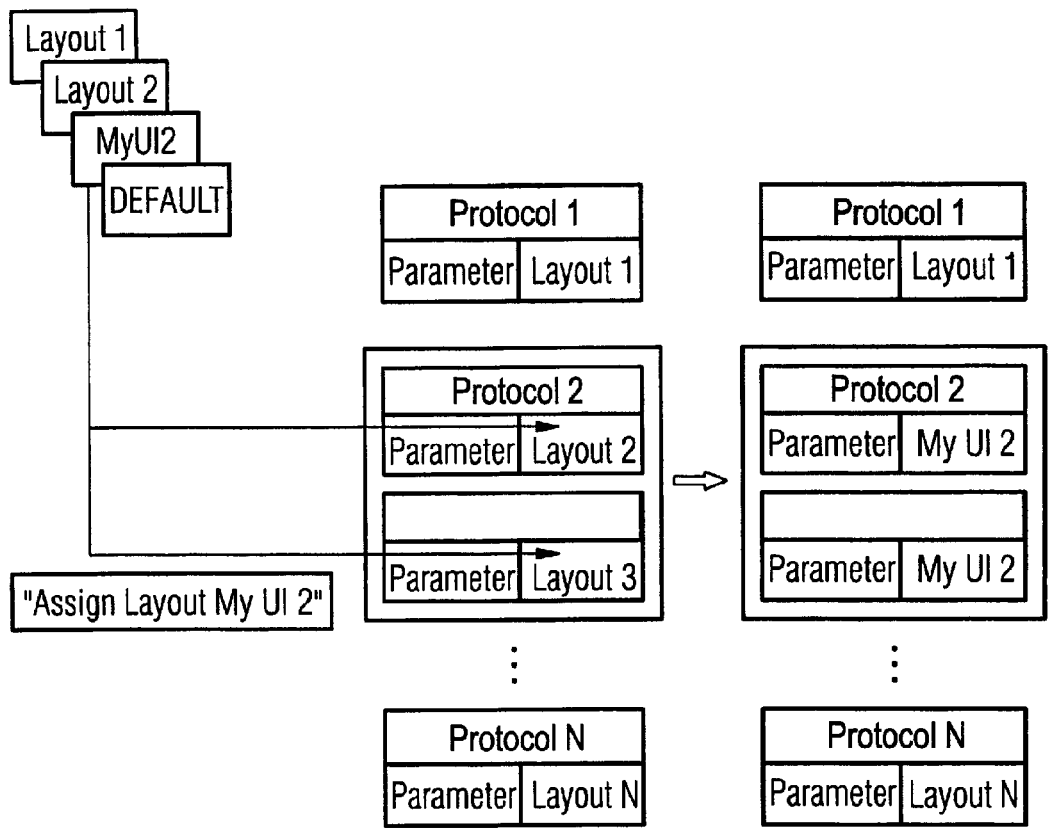
FIG. 2 shows an exemplary representation for a replacement of layout data of individual protocols, according to the invention.

The inventive replacement of previously set layout data with new layout data is shown again in FIG. 2. As indicated in FIG. 2, a specific layout is selected from centrally stored layout data (Layout 1, Layout 2, Layout 3, Default Layout) and associated with one or more protocols (the protocols 2 and 2 in FIG. 2) ("Assign Layout MyUI2"). This leads to the situation that the protocol 2 for which the Layout 2 previously applied and the protocol 3 for which the Layout 3 previously applied are replaced by the layout "MyUI2".

As mentioned above, the control elements S are parameter input options that normally comprise numerical parameter types (for example long, double), textual types (for example string) as well as parameters of the type "Bool", "Array", "Container parameter types". According to another aspect, other graphical representations of the parameter input options are conceivable such as, for instance, icon-based input options.

A fundamental concept of the present invention is that only basic information can be altered and stored in relative to the relevant control elements S, in particular parameters and parameter cards. However, the graphical details of the display on the screen furthermore remain subject to the implementation of the corresponding UI components. Thus the graphical "look and feel" of the user interface can remain constant for a specific software version and cannot be modified, so that the user does not have to readjust at the runtime of the respective application. According to the invention, only the selected control elements S relevant for a respective application are modifiable and storable. Thus only the parameters or the parameter cards are displayed that are also necessary for the application, in order to not burden the user with unnecessary auxiliary information and selection possibilities.

In an embodiment of the invention, the manner in which the control elements S should be displayed on the user interface BO can be set. For example, some control elements S can be represented in the form of a switch (as a Boolean parameter), or textually, or purely graphically. The respective graphical representation of the control elements S is configurable and can be set by the user.

If the card representation for the control elements S is selected, with corresponding sub-cards and sub-sub-cards, the names of the respective subordinate cards can thus be arranged as a title-like tab at the upper end of the card.

Figure 3:
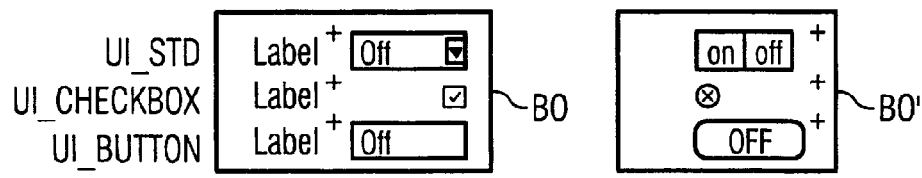
FIG. 3 shows an exemplary representation of different layouts for one and the same user interface according to the invention.

Two alternative embodiments of a user interface BO, BO' are presented in FIG. 3 based on the example of a switch parameter. Shown on the left side is a user interface BO that is based on a classical, textual layout, and shown on the right side is a user interface BO' that is based on an icon representation. To allow a change between these different designs, a presentation option is also provided for a card as a whole.

According to one embodiment, the inventive method has three different modes:
a DEFINE mode,
a USE mode and
an ASSIGN mode.

The DEFINE mode serves for interactive generation of a user interface BO; the USE mode applies this generated user interface and presents it on the screen; and the ASSIGN mode serves for association and storage of one or more layout(s) with one or more protocols. For the respective modes, activation and deactivation mechanisms are provided in order to activate or, respectively, to deactivate the respective modes. In the DEFINE mode the parameters that should appear on the new card are selected via selection on a previous card. Moreover, it is possible to shift the respective selected parameters to the new card to be generated or, respectively, to remove these again.

In the case described above, an existing layout is used in order to generate a new layout based thereupon. Alternatively, it is possible not to use an older, previous layout, but rather to generate the new layout manually through the explicit specification of the parameters. According to the invention it is typical that, given a repositioning of a control element S that occludes another control element S', a displacement of the respective control elements S, S' relative to one another is executed automatically so that no overlaps or superimpositions are generated. This advantageously ensues automatically.

In an embodiment of the invention, the new user interface BO to be generated is generated on the basis of the previous user interface. In other words, only the relevant control elements S and/or control groups are typically selected from the set of the previous control elements S and/or previous control groups. The non-relevant control elements S are not displayed on the user interface BO, but the previous order of the control elements S and/or of the control groups is thereby retained. Only individual parameters and/or parameter groups can thus be erased from the initial layout. In principle the user thereby does not need become reacquainted with the content.

In principle a newly defined layout can also be modified at a later point in time in that the DEFINE mode is returned to again.

In the USE mode a previously defined layout is selected to control the current visible cards. This typically ensues via the specification of a name associated with the layout. A representation corresponding to the selected layout thereupon ensues. If the USE mode is deactivated, the current parameters or parameter maps are again controlled via the layout data that are stored in the respective protocol.

With the ASSIGN mode it is possible to permanently associate a specific layout with one or more protocols. For this it is merely necessary to select the name of the respective layout from a list of possible layouts in the ASSIGN mode. The association ensues automatically. This selected layout then replaces the previous layouts for all selected protocols and is used to control the user interface BO.

FIG. 4 shows how a new interface BO' (shown below) with a new control element S should be generated based on an already existing interface BO (shown above). As long as the DEFINE mode is active (as shown in the upper, existing interface BO), this new sub-card appears in addition to the previously used cards. Like the others, the new card can also be opened in order to change details. It is likewise possible to adopt the control elements S unchanged into the new card. The corresponding data are then automatically transferred to the new card or, respectively, surface BO'. As shown on the lower, new card in FIG. 4, it is additionally possible to displace the respectively selected control elements S (parameters) or to remove these again from this card.

In FIG. 4 it is exemplarily shown how a new control element S is automatically displaced for a sub-card in the DEFINE mode such that no overlap with other control elements S ensues. A displacement and a deletion of individual parameters are thereby possible. The new parameters "TE . . . (ms)" can be displaced or erased in the sub-card (Sub-Card 1).

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a user interface for at least one medical imaging procedure, from among a plurality of medical imaging procedures, executable according to the user interface by a medical imaging apparatus, comprising the steps of:
   determining a medical imaging procedure, comprising acquisition of magnetic resonance image data to be implemented by a magnetic resonance imaging apparatus at a stationary location, for which a user interface is to be generated to allow a user to control, via the user interface, the imaging procedure by electronically operating the magnetic resonance imaging apparatus to cause the magnetic resonance imaging apparatus to execute a number of steps that form said imaging procedure;
   providing a designation of said medical imaging procedure as an input to a computerized processor and in said computerized processor, automatically identifying only control elements, for inclusion in said user interface as displayed control elements, that are relevant for controlling the determined magnetic resonance imaging procedure; and automatically grouping control elements, as grouped control elements among said displayed control elements that must be activated by the user in succession during said medical imaging procedure; and
   forming and configuring said user interface specifically for controlling said magnetic resonance apparatus to perform medical imaging procedure according to user interaction with said user interface and, from said computerized processor, automatically positioning said grouped control elements in said user interface on a display screen according to configurable positioning criteria that minimize space on said display screen occupied by said control elements, and said user interaction to activate said grouped control elements.

2. A method as claimed in claim 1 comprising employing graphical representations for respective parameter inputs as said control elements.

3. A method as claimed in claim 1 comprising positioning said control elements in a control group formed as a card.

4. A method as claimed in claim 1 comprising generating a reference and associating said reference with a user interface generated for a specific medical application of said medical imaging procedure, and using said reference to retrieve said user interface for subsequent use upon subsequent execution of said specific medical application.

5. A method as claimed in claim 1 comprising generating respective user interfaces for a set of different medical imaging procedures.

6. A method as claimed in claim 1 comprising generating said user interface by modifying an existing user interface comprising existing control elements, by automatically performing at least one action selected from the group consisting of shifting a position of at least one existing control element, deleting at least one existing control element, and adding a new control element.

7. A method as claimed in claim 6 comprising simulating said existing user interface and performing said action on the simulated existing user interface.

8. A method as claimed in claim 1 comprising, at run time of the medical application for which said user interface has been generated permitting a change from the generated user interface to a different user interface.

9. A method as claimed in claim 1 comprising generating said user interface with said control elements hierarchically structured and comprising sub-control elements.

10. A method as claimed in claim 1 comprising registering said control elements completely automatically.

11. A method as claimed in claim 1 comprising presenting the generated user interface at a display associated with said magnetic resonance imaging apparatus at said stationary location.

12. A method as claimed in claim 1 comprising generating said user interface by grouping a plurality of said control elements that are relevant for said medical imaging procedure into a control group according to configurable structuring criteria.

13. A method as claimed in claim 1 comprising allowing a user to interface with said computerized processor to review and modify said user interface at said display screen.

14. A system for generating a user interface for at least one medical imaging procedure, from among a plurality of medical imaging procedures, executable according to the user interface by a magnetic resonance imaging apparatus, comprising:
   a determination module that determines a medical imaging procedure comprising acquisition of magnetic resonance image data to be implemented by a magnetic resonance imaging apparatus at a stationary location, for which a user interface is to be generated to allow a user to control, via the user interface, the imaging procedure by electronically operating the magnetic resonance imaging apparatus to cause the magnetic resonance imaging apparatus to execute a number of steps that form said medical imaging procedure;
   a registration module, provided with a designation of said medical imaging procedure, that automatically identifies only control elements, for inclusion in said user interface as displayed control elements, that are relevant for controlling the determined medical imaging procedure and automatically grouping control elements, as grouped control elements among said displayed control elements that must be activated by a user in succession during said medical imaging procedure; and a positioning module that at least semi-automatically positions said control elements on a display screen to form and configure said user interface specifically for controlling said medical imaging procedure according to user interaction with said user interface, according to configurable positioning criteria that minimize space on said display screen occupied by said control elements, and said user interaction to activate said grouped control elements.

15. A system as claimed in claim 14 wherein said positioning module is configured to allow user interaction with said display screen to modify said user interface at said display screen.

16. A non-transitory computer-readable storage medium encoded with a data structure for generating a user interface for at least one medical imaging procedure to be executed by a magnetic resonance imaging apparatus, said data structure, when said computer-readable medium is loaded into a computer, causing said computer to:

determine a medical imaging procedure to be implemented by the magnetic resonance imaging apparatus for which a user interface is to be generated to allow an operator to control, via the user interface, the medical imaging procedure being implemented by the magnetic resonance imaging apparatus to cause the magnetic resonance imaging apparatus to execute a number of steps that form said medical imaging procedure;

automatically identify only control elements, for inclusion in said user interface as displayed control elements, that are relevant for controlling the determined medical imaging procedure and automatically grouping control elements, as grouped control elements among said displayed control elements that must be activated by a user in succession during said medical imaging procedure; and automatically position said control elements individually or in groups on a display screen to form and configure said user interface specifically for controlling said medical imaging procedure according to user interaction with said user interface, according to configurable positioning criteria that minimize space on said display screen occupied by said control elements, and said user interaction to activate said grouped control elements.

17. A non-transitory computer-readable storage medium as claimed in claim 16 wherein said programming instructions further cause said computer to allow interaction with said user interface at said display screen to modify said user interface at said display screen.

* * * * *